United States Patent [19]
Wetterlin

[11] Patent Number: 5,983,893
[45] Date of Patent: *Nov. 16, 1999

[54] INHALATION DEVICE

[75] Inventor: Kjell Wetterlin, Södra Sandby, Sweden

[73] Assignee: Astra Aktiebolag, Sodertalje, Sweden

[ * ] Notice: This patent issued on a continued prosecution application filed under 37 CFR 1.53(d), and is subject to the twenty year patent term provisions of 35 U.S.C. 154(a)(2).

[21] Appl. No.: 08/663,266

[22] PCT Filed: Dec. 19, 1995

[86] PCT No.: PCT/SE95/01539

§ 371 Date: Jun. 19, 1996

§ 102(e) Date: Jun. 19, 1996

[87] PCT Pub. No.: WO96/19253

PCT Pub. Date: Jun. 27, 1996

[30] Foreign Application Priority Data

Dec. 21, 1994 [SE] Sweden .................................. 9404439

[51] Int. Cl.⁶ .................................................. A61M 16/00
[52] U.S. Cl. ................................ 128/203.15; 128/203.12; 128/200.14; 128/203.21; 128/200.21
[58] Field of Search .......................... 128/203.15, 200.11, 128/200.14, 200.21, 200.22, 203.12, 203.19, 203.28, 205.13, 203.21, 203.23, 203.24

[56] References Cited

U.S. PATENT DOCUMENTS

| | | | |
|---|---|---|---|
| 2,570,774 | 10/1951 | Danvis | 128/203.15 |
| 2,581,182 | 1/1952 | Fields | 128/203.15 |
| 2,642,063 | 6/1953 | Brown | 128/203.15 |
| 3,658,059 | 4/1972 | Steil | |
| 3,838,686 | 10/1974 | Szekely | |
| 4,344,573 | 8/1982 | De Felice | 128/203.15 |
| 4,368,850 | 1/1983 | Szekely | 239/333 |
| 4,524,769 | 6/1985 | Wetterlin | 128/203.15 |
| 4,690,332 | 9/1987 | Hughes | 128/200.21 |
| 4,907,583 | 3/1990 | Wetterlin et al. | 128/203.15 |
| 4,940,051 | 7/1990 | Lankinen | 128/203.15 |
| 4,955,371 | 9/1990 | Zamba et al. | 128/200.21 |
| 4,972,830 | 11/1990 | Wong et al. | 128/200.21 |
| 5,033,463 | 7/1991 | Cocozza | 128/203.15 |
| 5,056,511 | 10/1991 | Ronge | 128/203.12 |
| 5,062,419 | 11/1991 | Rider | 128/200.14 |
| 5,069,204 | 12/1991 | Smith et al. | 128/203.12 |
| 5,239,992 | 8/1993 | Bougamont et al. | 128/203.15 |
| 5,341,801 | 8/1994 | Zechner | 128/203.15 |
| 5,507,281 | 4/1996 | Kuhnel et al. | 128/203.15 |
| 5,579,760 | 12/1996 | Kohler | 128/203.15 |
| 5,584,288 | 12/1996 | Baldwin | 128/203.11 |
| 5,623,920 | 4/1997 | Bryant | 128/200.19 |

FOREIGN PATENT DOCUMENTS

| | | |
|---|---|---|
| 0 069 715 B1 | 11/1986 | European Pat. Off. . |
| 384050 A1 | 8/1990 | European Pat. Off. . |
| 0 237 507 B1 | 12/1991 | European Pat. Off. . |

*Primary Examiner*—John G. Weiss
*Assistant Examiner*—V. Srivastava
*Attorney, Agent, or Firm*—Fish & Richardson P.C.

[57] ABSTRACT

An inhalation device for inhalation of a pharmaceutically active substance from a reservoir in an inhaler comprising an inhalation channel with an air inlet and an air outlet, said device comprising a dispersing chamber having an air inlet and an air outlet into which the active substance may be sucked from said reservoir through the air outlet and means for allowing a user to inhale the active substance from said dispersing chamber, said dispersing chamber being defined by at least a first non-movable element and a second movable element, said second element being substantially cylinder-formed, said first element being arranged in said second element whereby a vacuum or negative pressure is created in said dispersing chamber when said first and second elements are moved in relation to each other, wherein said first non-movable element is fixed on the inhaler so that the second element will move in relation to both the first element and the inhaler when the device is activated for inhalation. The invention also relates to a method of dispersing a pharmaceutically active substance in a dispersing chamber by creating a negative pressure or vacuum in said dispersing chamber.

26 Claims, 2 Drawing Sheets

INHALATION DEVICE

This application is a 371 of PCT/SE 95/01539 filed Dec. 12, 1995.

The present invention relates to an inhalation device for inhalation of a pharmaceutically active substance from a reservoir in an inhaler comprising an inhalation channel with an air inlet and an air outlet, said device comprising a dispersing chamber having an air inlet and an air outlet into which the active substance may be sucked from said reservoir through the air outlet and means for allowing a user to inhale the active substance from said dispersing chamber, said dispersing chamber being defined by at least a first non-movable element and a second movable element, said second element being substantially cylinder-formed, said first element being arranged in said second element whereby a vacuum or negative pressure is created in said dispersing chamber when said first and second elements are moved in relation to each other.

The inhalation device according to the invention is preferably a breath-actuated dry-powder inhaler, containing multiple doses of a medicament containing an active substance, the inhaler having maneuvering unit for loading one dose of the medicament to a dosing unit and providing said dose in a position for inhalation. An inhaler of the prescribed type is described in EP-A-0 069 715 and EP-A-0 237 507.

The device according to the invention is especially designed for patients who are not able to actively inhale or who are not able to create the inhalation flow necessary to release and lift the dose of the substance into the inhalation channel and to the lungs when using a breath-actuated inhaler.

BACKGROUND OF THE INVENTION

Inhalable pharmaceutically active substances are generally used for treatment of diseases in the bronchial and pulmonary area, such as asthma and chronic bronchitis. Various embodiments of inhalation devices or apparatus are used for the purpose. The function of these known devices depends on the creation of an airflow through the inhalation device caused by an inhalation by the patient. The airflow causes active substance to moved from a release position into the airflow in which it is dispersed. A specially advantageous inhaler of the above mentioned type is the dry-powder, breath-actuated multidose inhaler TURBUHALER®, schematically described in the above mentioned EP-patents.

Some patients such as small children and elderly people with diseases in the bronchial area are not able to use a breath-actuated inhaler as it might be hard or even impossible for these patients to achieve the necessary inhalation flow and these patients are today reduced to the use of inhalers using pressurized gas, i.e. freon. Such inhalers suffer from many known disadvantages, such as unwanted side effects.

Furthermore, it is presently a problem to administer an Inhalable substance to an asthma patient who is anesthetized during an operation and the patient can not actively inhale. For many asthmatic patients the administration of asthma pharmaceuticals during an operation is vital.

PRIOR ART

In order to facilitate the inhalation of pharmaceutically active substances being administered by the use of pressurized metered dose inhalers, so called PMDIs, it is known to provide expansion chambers into which the substance, with the pressurized gas, is dispersed. These devices are generally called spacers and a typical spacer is known from GB 1 565 029.

Furthermore, inhalation devices including dispersion chambers have been developed for breath-actuated dry-powder inhalers of the above mentioned type. Such an inhalation device is described in EP-A-0 548 152. This device is however bulky and contains several mechanical parts which makes the device complicated and expensive to produce and to use. The reliability is not very high due to the complexibility of the device.

SUMMARY OF THE INVENTION

The present invention relates to an inhalation device of the above mentioned type which can be used by patients having reduced ability to create an inhalation flow necessary to lift the dose from the release position into the inhalation channel when using a breath-actuated inhaler, and which can be used to administer Inhalable substances to a patient being anesthetized.

The invention provides a device which facilitates the use of especially a TURBUHALER® for patients presently being reduced to the use of pressurized metered-dose inhalers.

The inhalation device according to the invention has a non-complicated construction with few mechanical parts, is simple and cheap to produce and is easy to use by the patient.

In the device according to the invention a first non-movable element is fixed on the inhaler so that a second element will move in relation to both the first element and the inhaler when the device is activated for inhalation.

Further advantages with the present invention are clear form the depending claims 2 to 16.

The present invention also includes a method of dispersing a pharmaceutically active substance, in a dispersing chamber by creating a negative pressure or vacuum in said dispersing chamber by using a device according to the invention. The dispersed substance could thereby be inhaled using an ordinary inhalation flow or it could be pressed out from the inhalation device.

BRIEF DESCRIPTION OF THE DRAWINGS

The inhalation device according to the present invention will now be described by way of example with reference to the appended drawings, in which.

DETAILED DESCRIPTION OF THE DRAWINGS

The device according to the invention is intended to be used in connection with an inhaler for inhalation of a pharmaceutically active substance, e.g. the breath-actuated, dry-powder, multidose inhaler 12 sold under the trademark TURBUHALER® . The inhalation device according to the invention may be modified within the scope of the appended claims to be used with any dry-powder inhaler which when activated positions a dose of the medicament in a release position in the inhalation channel.

Figure 1:
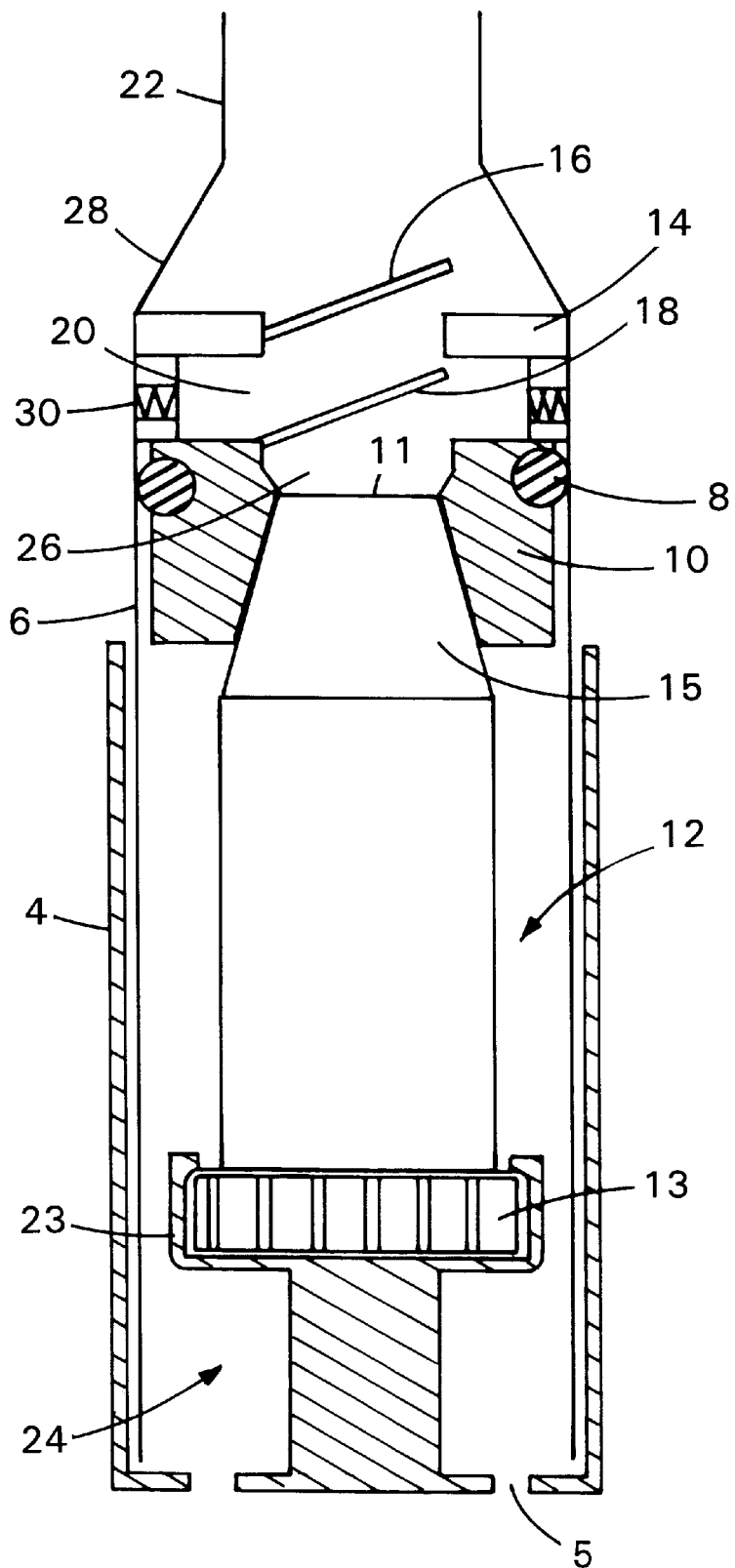
FIG. 1 shows a schematic view of a section of the inhalation device according to a first embodiment of the invention.
Figure 2:
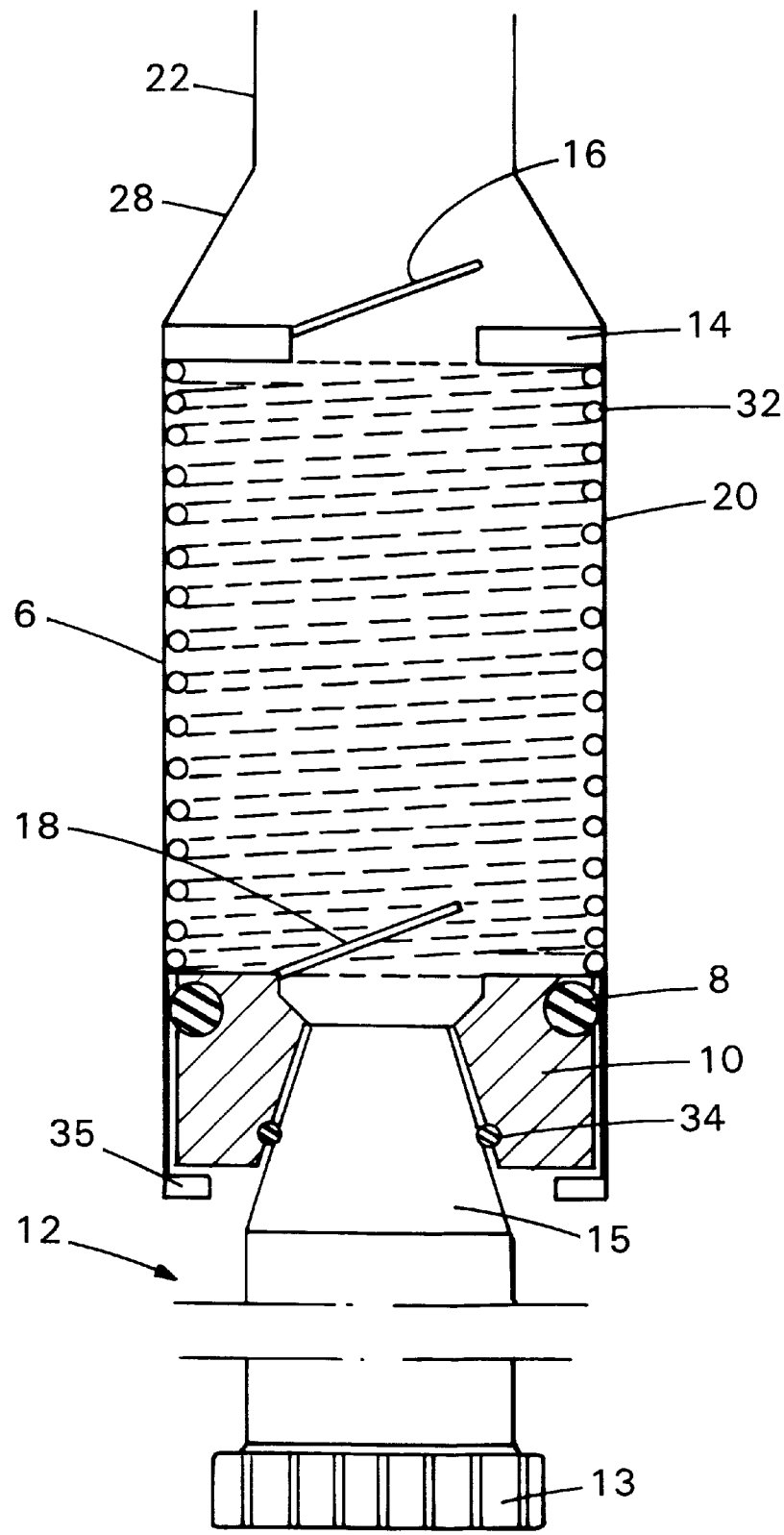
FIG. 2 shows a schematic view of a section of the second embodiment of the inhalation device according to the invention.

Referring to FIG. 1, the preferred inhaler 12 is provided with a reservoir for storing the substance, a metering or dosing unit, and an inhalation channel having an air inlet and an air outlet. The inhaler is also provided with operating means comprising a maneuvering unit 13 for moving a metering device from a loading position in which a predetermined dose of the substance to be inhaled is metered into the metering device and a release position where the dose is placed in the inhalation channel, released and carried by the inhalation air through the channel to the air outlet or mouthpiece 15 of the inhaler.

As can be seen in the drawings the inhalation device according to the invention comprises a first substantially non-moving element 10 which is provided on the air outlet or mouth piece 15 of the inhaler. The first element 10 is formed as a piston having an opening 26 which, when the piston is arranged on the air outlet of the inhaler, coincides with the opening 11 of the air outlet. The connection between the air outlet or mouth piece 15 of the inhaler and the piston is air tight through a sealing or as in the preferred embodiment the piston is rigidly mounted on the outer walls of the air outlet or mouth piece 15 of the inhaler in order to prevent air from entering between the two parts. The piston could be glued, welded or rigidly fastened in any other manner to the inhaler.

Around said first substantially non-moving element, i.e. the piston 10, a movable second element 6 is provided. Said second element 6 is hollow and substantially formed as a cylinder. In the upper part of the cylinder the walls merge and define a cone-shaped part 28. Above this cone-shaped part 28 a further cylinder 22 having a smaller diameter than the cylinder 6 defining the second element is arranged. Said cylinder 22 defines the air outlet of the dispersing chamber 20 and the inhalation device and is formed as a mouth piece or nose adapter part.

The piston 10 is arranged inside the cylinder 6. The piston thereby defines the bottom of the second element 6. A dispersing chamber 20 is defined in the cylinder 6 above the piston 10. Sealing means 8 are provided between the first and second elements at their mutual area of connection. The sealing means 8 are preferably provided as an O-ring sealing member and could be arranged in a groove provided on the outer surface of the piston.

As mentioned above the piston 10 is formed with an opening 26 which coincides with the opening 11 of the air outlet or mouth piece 15 of the inhaler. First valve means 18 are provided regulating the air flow through the air outlet and the opening in the piston to the dispersing chamber 20. The valve means are provided as a one way valve arranged to only open when the air flows from the inhaler to the dispersing chamber. The valve could be of any known type and is in the preferred embodiment formed as a thin membrane of which one part is fixed to the wall of the piston and the other end is free moving.

The cylinder 6 is formed with a limiting wall member 14 having an outlet opening coinciding with the air outlet of the inhaler. The wall member 14 defines the upper restriction of the dispersing chamber 20 and is provided with holding means 30 for holding the inhaler in a fixed position in relation to the rotation when the maneuvering unit 13 is rotated. These means could be provided as a ratchet mechanism, as teeth rings or have any other construction. Second valve means 16 are provided in said opening for regulating the air flow out from the dispersing chamber upon inhalation of a user. A mouth piece 22 or nose adapter is provided at the end of the cylinder 6.

The first and second valves 18 and 16 are preferably of similar construction and must be sensitive and easy to open in order to minimize the inhalation flow resistance and retention of substance within the inhalation device. For this purpose the valves could preferably be made as thin membranes of plastic or the like. The membranes could be fixed at one end in the opening of the piston 10 and the wall member 14 respectively, as can be seen in the figure. The wall member 14 acts as a valve seat for the valve 18.

In a first preferred embodiment a further hollow cylinder element 4 is provided. The cylinder is defined by a bottom and wall parts and is opened in its upper region. The bottom of said further cylinder 4 is provided with air inlet openings 5 communicating with the inside of said further cylinder element 4. A mounting element 24 for the inhaler is provided inside said further cylinder and fixed to the bottom of the cylinder. The mounting element 24 comprises a portion 23 adapted to the form of the maneuvering unit 13 of the inhaler in order for it to be fixedly mounted in said mounting means 24.

Due to this fixed and rigid mounting of the maneuvering unit 13 of the inhaler 12 in the mounting part 23 the unit 13 is rotated an angle proportional to the rotation of the outer cylinder-formed element 4. The rotation of the outer cylinder-formed element 4 and thereby the maneuvering unit 13 activates the inhaler 12 for inhalation as the maneuvering unit places the dosing unit and thereby a dose in the release position within the inhalation channel.

The function of this embodiment will now be described.

In the inactive position, which is shown in FIG. 1, the inner cylinder-formed element 6 is totally interposed into the outer cylinder-formed element 4. When the outer element 4 is turned the maneuvering unit 13 and the dosing unit of the inhaler is turned and a dose is placed in release position in the inhalation channel. The two cylinder formed elements 4 and 6 are thereafter moved axially in relation to each other whereby the inhaler 12 with the piston 10 is pressed downwards along the inner wall of the inner element 6. A low-pressure or vacuum is created in the dispersing chamber 20 when the elements are moved away from each other. The second valve 16 closes.

The valve 18 opens and air is drawn into the inhalation device through the air inlets 5 in the bottom part of the outer element 4. When the air passes the inhaler, the dose placed in the inhalation channel is released and dispersed into the dispersing chamber 20.

The dispersed substance can now be actively inhaled by the patient, a method which could be used also by small children, elderly people and others with reduced inhalation capacity .

Alternatively the substance can be forced out of the dispersing chamber 20 by pressing the piston 10 and the second element 6 together again after the activation and dispersion of the dose has taken place. The volume in the dispersing chamber will then decrease and an over pressure or positive pressure will be created. The valve 18 will open and air/substance contents of the dispersing chamber 20 will be forced out through the mouth piece 22 of the device. In this manner substance can be forced down into the lungs of the patient. This active pressing out of the substance is especially intended to be used when treating an anesthetized patient but could also be used under other circumstances, e.g. by small children or elderly people refusing to inhale.

Referring to FIG. 2, the inhalation device could also be constructed without the outer cylinder 4.

A biasing element 32 is thereby provided between the piston 10, which is mounted on the mouthpiece and/or upper part of the inhaler, and the cylinder 6. The cylinder 6 is provided with stop means 35 provided at the opened end of the cylinder preventing the cylinder from being separated from the piston 10. Further sealing means 34 are provided between the piston 10 and the inhaler 12. In this embodiment in the inactivated position of the device the piston 10 is arranged in relation to the cylinder in such a manner that the dispersing chamber has its largest volume, i.e. the piston and the cylinder are in the retracted position in relation to each other. When the device is activated for inhalation a dose is placed in the inhalation channel by the rotating movement of the maneuvering unit 13, which in this embodiment is handled directly by the user. The piston 10 is then moved within the cylinder 6, i.e. the piston is pushed towards the outlet of the cylinder 6, against the force of the biasing element 32. The volume of the dispersing chamber is decreased. The piston 10 is then released and will due to the force of the biasing element travel instantly towards the bottom of the cylinder thereby creating a negative pressure or vacuum in the dispersing chamber as the volume increases. The dose will be sucked with the air entering into the air inlets of the inhaler to the inhalation channel and further up to the dispersing chamber. When the pressure has been compensated the valve 18 will close and the user can inhale through the mouth piece as described above.

Further sealing means could be provided in order to secure an airtight sealing between the inhaler 12, the piston 10 and the cylinder 6.

The biasing element 32 is preferably a spiral spring but any other type of resilient element could be used.

The use of the device to force the dose to be inhaled down into the lungs of a patient as described above could of course also be used with a device constructed in accordance with the second embodiment of the invention.

The volume of the spacer could be varied due to requirements and needs, and a preferred maximum volume of the dispersing chamber is between 50–250 ml.

The different parts of the inhalation device are preferably made of plastics, metallized plastics or metal but other materials are also possible.

The present invention is preferably directed to the use of a pharmaceutically active substance in powdered form wherein the powder is dispersed into the dispersing chamber 20 of the inhalation device in a finely divided form wherein the particles are smaller than 10 $\mu$m, preferably smaller than 3 $\mu$m.

POSSIBLE MODIFICATIONS OF THE INVENTION

The inhalation device according to the present invention could be modified within the scope of the appended claims.

In the preferred embodiment the means for generating the negative pressure or vacuum are two cylinder-formed elements provided telescopically in relation to each other. In the preferred embodiment the elements have a circular cross-section but any other form such as squared is possible.

In the second embodiment a further cylinder could be provided in the second element 6. Said further cylinder is arranged to be separately movable in relation to the second element 6, whereby the biasing means are provided in a space between the two cylinders.

I claim:

1. An inhalation device for connection to an inhaler having a pharmaceutically active substance in a reservoir of said inhaler when connected to the inhalation device, the device comprising:

a first element that has connecting structure adapted to be connected to the inhaler, such that air drawn from the air outlet of the inhaler passes through said first element;

a second element slidably connected to said first element;

a dispersing chamber, defined by said first element and said second element and having a outlet with a valve element permitting flow of air and said substance out of said chamber to a patient but preventing flow of air into said chamber, the relative movement of said first element and said second element being capable of increasing the volume of said dispersing chamber and decreasing pressure by closing said valve element therein so as to draw air through and from said inhaler with said substance entrained therein into said dispersing chamber.

2. The inhalation device of claim 1, further comprising a sealing member to create a seal between said first element and said second element.

3. The inhalation device of claim 1 wherein said connecting structure of said first element has an opening sized and shaped to mate with the air outlet of the inhaler to which the air outlet of the inhaler is fitted with an air-tight seal.

4. The inhalation device of claim 3 wherein the opening in said first element is in direct alignment with an opening of the air outlet of the inhaler.

5. The inhalation device of claim 1, further comprising a first valve connected to said first element, said first valve designed to open when the relative movement of said first element and said second element creates a decrease in pressure in said dispersing chamber and air is drawn through the inhaler into said dispersing chamber, said first valve being designed to close when the relative movement of said first element and said second element creates an increase in pressure in said dispersing chamber.

6. The inhalation device of claim 1 wherein the inhaler is a conventional dry-powder inhaler.

7. The inhalation device of claim 6 wherein the inhaler has a manoeuvering apparatus, said manoeuvering apparatus including a dosing unit and a dosing disc, for feeding a dose of the pharmaceutically active substance from a loading position to a position for inhalation in the inhalation channel of the inhaler.

8. The inhalation device of claim 7 wherein the breath-actuated dry-powder inhaler is a TURBUHALER inhaler.

9. The inhalation device of claim 1 wherein the first element is rigidly mounted on the air outlet of the inhaler.

10. The inhalation device of claim 7, further comprising a sleeve surrounding said second element, said sleeve being rotatable relative to said second element, and said sleeve capable of being connected to the inhaler.

11. The inhalation device of claim 10 wherein the manoeuvering apparatus is fixedly connected to said sleeve, so that rotation of said sleeve relative to said second element causes rotation of the manoeuvering apparatus of the inhaler and positions a dose of pharmaceutically active substance for inhalation.

12. The inhalation device of claim 1, further comprising a biasing element between said first element and said second element.

13. The inhalation device of claim 12 wherein said biasing element is a spiral spring.

14. The inhalation device of claim 1 wherein said first element is in the form of a piston.

15. The inhalation device of claim 2 wherein said sealing member is an O-ring.

16. The inhalation device of claim 15 wherein said O-ring sealing member is arranged in a circular groove provided along an outer surface of said first element.

17. The inhalation device of claim 1, further comprising a final air outlet through which a user may access air with said pharmaceutically active substance entrained therein from said dispersing chamber.

18. The inhalation device of claim 17 wherein said final air outlet of the device comprises a mouth piece or nose adapter.

19. The inhalation device of claim 17 wherein a further conical region connects said dispersing chamber to said final air outlet.

20. The inhalation device of claim 3 wherein said opening of said first element sized and shaped to mate with the air outlet of the inhaler has a generally conical shape.

21. An inhalation device for connection to an inhaler having a pharmaceutically active substance in a reservoir of said inhaler when connected to the device, the device comprising:

a first element that is connected to the inhaler, such that air drawn from the air outlet of the inhaler passes through said first element;

a second element slidably connected to said first element;

a dispersing chamber, defined by said first element and said second element, the relative movement of said first element and said second element being capable of increasing the volume of said dispersing chamber and decreasing pressure therein so as to draw air with said substance entrained therein from said inhaler into said dispersing chamber;

a first valve connected to said first element, said first valve designed to open when the relative movement of said first element and said second element creates a decrease in pressure in said dispersing chamber and air is drawn through the inhaler into said dispersing chamber, said first valve being designed to close when the relative movement of said first element and said second element creates an increase in pressure in said dispersing chamber;

a second valve connected to said second element, said second valve designed to close when the relative movement of said first element and said second element creates a decrease in pressure in said dispersing chamber and air is drawn through the inhaler into said dispersing chamber, said second valve being designed to open when the relative movement of said first element and said second element creates an increase in pressure in said dispersing chamber.

22. The inhalation device of claim 21 wherein said first and second valves are designed to open when a user draws a breath through the air outlet of the inhaler.

23. The inhalation device of claim 22 wherein said first and second valves are formed as thin membranes fixed at one end to said first element and said second element, respectively, and freely moveable at the other end.

24. A method of preparing a dose of pharmaceutically active powdered substance for inhalation therapy comprising the steps of:

providing an inhaler, said inhaler containing the pharmaceutically active powdered substance;

providing an inhalation device, said inhalation device having a first element that has connecting structure adapted to be attached to said inhaler, a second element slidably connected to said first element, a dispersing chamber defined by said first element and said second element, and an outlet with a valve element permitting flow of air and said substance out of said chamber to a patient but preventing flow of air into said chamber;

connecting said inhaler to said inhalation device;

moving said first element and said second element relative to each other so that the volume of said dispersing chamber increases and creates a decrease in pressure by closing said valve element therein, which decrease in pressure draws air through and from the inhalation channel and activates said inhaler, thereby dispersing the pharmaceutically active powdered substance in said dispersing chamber.

25. The method of claim 24, further comprising the step of forcing the air and the dispersed pharmaceutically active powder out of the inhalation device through said mouthpiece.

26. The method of claim 25 wherein the step of forcing the air and dispersed pharmaceutically active powder out of the inhalation device through said mouthpiece is achieved by moving said first element and said second element relative to each other so that the volume of said dispersing chamber decreases and creates a positive pressure therein.

\* \* \* \* \*